United States Patent
Peters et al.

(10) Patent No.: US 11,179,407 B2
(45) Date of Patent: Nov. 23, 2021

(54) METHOD FOR SYNTHETICALLY PRODUCING ARABINOGALACTAN COMPOUNDS DERIVED FROM PLANTS AND USES OF SAID COMPOUNDS FOR THE PROPHYLAXIS OF ALLERGIC REACTIONS

(71) Applicants: Forschungszentrum Borstel Leibniz-Zentrum für Medizin und Biowissenschaften, Borstel (DE); Universität Rostock, Rostock (DE); Ruhr-Universität Bochum, Bochum (DE)

(72) Inventors: Marcus Peters, Haltern (DE); Otto Holst, Bad Oldesloe (DE); Christian Vogel, Elmenhorst/Lichtenhagen (DE); Alice Voss, Moltenow (DE)

(73) Assignees: FORSCHUNGSZENTRUM BORSTEL LEIBNIZ-ZENTRUM FÜR MEDIZIN UND BIOWISSENSHAFTEN, Borstel (DE); UNIVERSITÄT ROSTOCK, Rostock (DE); RUHR-UNIVERSITÄT BOCHUM, Bochum (DE)

( * ) Notice: Subject to any disclaimer, the term of this patent is extended or adjusted under 35 U.S.C. 154(b) by 493 days.

(21) Appl. No.: 15/779,745

(22) PCT Filed: Nov. 30, 2016

(86) PCT No.: PCT/EP2016/079189
§ 371 (c)(1),
(2) Date: May 29, 2018

(87) PCT Pub. No.: WO2017/093276
PCT Pub. Date: Jun. 8, 2017

(65) Prior Publication Data
US 2020/0306279 A1    Oct. 1, 2020

(30) Foreign Application Priority Data
Dec. 1, 2015  (EP) .................................... 15197381
Dec. 4, 2015  (EP) .................................... 15198104

(51) Int. Cl.
| | |
|---|---|
| A61K 31/7028 | (2006.01) |
| A61K 47/64 | (2017.01) |
| A61P 37/08 | (2006.01) |
| A61P 29/00 | (2006.01) |
| A61K 9/00 | (2006.01) |
| A61K 35/744 | (2015.01) |
| A61K 35/745 | (2015.01) |
| C07H 15/04 | (2006.01) |

(52) U.S. Cl.
CPC ........ *A61K 31/7028* (2013.01); *A61K 9/0043* (2013.01); *A61K 35/744* (2013.01); *A61K 35/745* (2013.01); *A61K 47/643* (2017.08); *A61P 29/00* (2018.01); *A61P 37/08* (2018.01); *C07H 15/04* (2013.01)

(58) Field of Classification Search
None
See application file for complete search history.

(56) References Cited

FOREIGN PATENT DOCUMENTS

| | | |
|---|---|---|
| WO | 2006025068 A1 | 3/2006 |
| WO | 2010020379 A1 | 2/2010 |

OTHER PUBLICATIONS

Wong, Current Opinion in Structural Biology 1995, 5:599-604. (Year: 1995).*
Sahloul, J. Org. Chem. 2015, 80, 11417-11434, published Oct. 28, 2015. (Year: 2015).*
Kandasamy, J. et al., "Automated solid phase synthesis of oligoarabinofuranosides." Chem. Common., 2013, 49(40): 4453-4455.
Lambden, P. R., Heckels, J. E., "Synthesis of immunogenic oligosaccharide-protein conjugates from the lipopolysaccharide of Neisseria gonorrhoeae P9." J. Immunol. Methods, 1982,48 (2): Abstract.

* cited by examiner

*Primary Examiner* — Layla D Berry
(74) *Attorney, Agent, or Firm* — Saliwanchik, Lloyd & Eisenschenk

(57) ABSTRACT

The present invention relates to L-arabino-oligosaccharides, in particular synthetically produced L-arabino-oligosaccharides and their uses for the prophylaxis of allergic reactions in mammals.

10 Claims, 6 Drawing Sheets

PS-BSA

Ara-BSA

METHOD FOR SYNTHETICALLY PRODUCING ARABINOGALACTAN COMPOUNDS DERIVED FROM PLANTS AND USES OF SAID COMPOUNDS FOR THE PROPHYLAXIS OF ALLERGIC REACTIONS

CROSS REFERENCE TO RELATED APPLICATIONS

This application is a National Stage Application of International Application Number PCT/EP2016/079189, filed Nov. 30, 2016; which claims priority to European Patent Application No. 15197381.5, filed Dec. 1, 2015 and European Patent Application No. 15198104.0, filed Dec. 4, 2015.

The present invention relates to L-arabino-oligosaccharides, in particular synthetically produced L-arabino-oligosaccharides, and their uses for the prophylaxis of allergic reactions in mammals.

BACKGROUND OF THE PRESENT INVENTION

Epidemiologic studies showed that children that grow up in the traditional environment of farms exhibit protection against the development of atopic diseases, such as, for example, allergic asthma bronchiale (Riedler et al. 2001, Braun-Fahrländer et al. 2002). It was assumed that the allergy protection is caused by inhalation of dusts in the stables of the farms.

When searching for the protective substances in the stables, it could be shown that this effect can be mediated by immune-modulatory "cowshed dust extract" (CDE). It was found in a mouse-asthma model that the inhalation of CDE causes a protective effect both regarding the development of bronchial hyperreactivity and the eosinophilia in the airways. The CDE also showed an immune-modulatory effect on human dendritic cells (DC), causing a reduced T-cell-stimulatory capacity in allogenic cocultures (Peters et al. 2006). In order to then identify the nature of the immune-modulatory molecules, the extract was characterized for its chemical composition, and arabinogalactan could be isolated as one of the active substances from the dusts, which primarily consisted of plant material. WO 2010/020379 discloses the structure of the arabinose-side chains of the arabinogalactan as identified.

It is thought that arabinogalactan in the dust has its origin in the plant matter used to feed livestock, as this is commonly stored in stables. In line with this, arabinogalactan could also be isolated from plants like meadow foxtail (fodder), timothy grass, and bluegrass.

Additional experiments then showed that plant-derived arabinogalactan induces autocrine IL-10-production in murine dendritic cells. Because of the autocrine tolerization as caused by the IL-10, these DC are no longer able to produce an allergic immune response. This showed that the allergic protection as induced by arabinogalactan is mainly due to the reduction of the Th2-inducing effect of dendritic cells.

Arabinogalactan-Proteins (AGP) are commonly found in the plant kingdom, and are essentially macromolecules of polysaccharides in which the carbohydrate is associated with or linked to proteins. AGP is composed mainly of arabinose and galactose residues. These occur in plants as polysaccharides in association with varying amounts of proteins, and generally contain a high proportion of carbohydrates with comparatively less proportion of proteins, usually less than 10% of proteins, although, AGPs having higher contents of proteins are also known.

WO 2006/025068 discloses a purified arabinogalactan-protein (AGP) composition, having an average molecular weight range between 10 KD to 150 KD, isolated from the leaves and/or stems of *Argemone mexicana*.

Currently, there is no possibility for an effective prophylaxis of allergic diseases. The use of arabinogalactans could be a promising approach. Nevertheless, because of the size and complexity thereof, functional molecules cannot be synthetically produced. Isolating the molecules from natural sources is quite laborious, and production on an industrial scale can only be achieved with both high financial and technical investments. Furthermore, contamination with other immunomodulatory molecules after laborious purification-procedures could not be excluded.

It is therefore an object of the present invention, to resolve the above problems, and to provide novel and effective pharmaceutical drugs for the prophylaxis of allergic reactions, and preferably allergic asthma in mammals, and in particular humans. Other objects and advantages of the present invention will become apparent to the person of skill when studying the specification of the present invention.

In a first aspect thereof, the object of the present invention is solved by providing an L-arabino-oligosaccharide, in particular a synthetically produced L-arabino-oligosaccharide according to the following general formula (I)

(I)

wherein the arabino-configured monosaccharides are either α- or β-connected. In the above formula, R is selected from a linker group Z according to the following formula wherein X can be selected from O, S, $CH_2$, and $PO_4^-$; and wherein Y can be selected from $NH_2$, $CO_2H$, wherein V is selected from a $C_1$-$C_6$ alkyl or aryl residue; a D-galactose residue comprising Z, and a β-(1→6)-linked D-galactose oligosaccharide comprising Z, and wherein Z is optionally coupled to a proteinaceous group P, and pharmaceutically acceptable salts thereof.

The pharmaceutical acceptable salts are salts commonly used in pharmaceutical preparations, for example, the sodium salt, calcium salt, potassium salt, or chloride salt.

Structurally, arabinogalactan consists of a backbone of galactose comprising numerous substitutions with arabinose-side chains in different configurations. Experiments, where the arabinose side chains were split off from the core molecule seem to show that the immune-modulatory and the allergy-protective effects of arabinogalactan are related to the arabinose residues on the surface. Following chemical removal of the arabinose, a large portion of the allergy-protective effect of the molecule is lost (Peters et al. 2010).

Preferred is the arabino-oligosaccharide according to the present invention, wherein R is selected from the groups of wherein Z is as defined herein.

Further preferred is the arabino-oligosaccharide according to the present invention according to the following general formula (II)

(II)

wherein Z is as defined herein, and pharmaceutically acceptable salts thereof. A particularly preferred embodiment is the arabino-oligosaccharide according to the present invention according to the following formula and pharmaceutically acceptable salts thereof.

In the context of the present invention, a partial structure of the arabinogalactan was synthetically produced. In this embodiment, the oligosaccharide consisted of three molecules galactose and two molecules arabinose. This compound was then covalently coupled to a carrier protein, such as albumin. The use of oligosaccharides having a defined structure that are coupled to proteins is a new approach for the prevention of allergic diseases.

In another preferred aspect of the arabino-oligosaccharide according to the present invention, the arabino-oligosaccharide is complexed and/or covalently coupled to a carrier protein P, such as albumin. The carrier protein can be readily selected by the person of skill and is selected from a group of proteins that contain more than one primary amine on the surface, hence giving the opportunity to bind multiple oligosaccharides to the surface of the protein. This provides the basis for crosslinking of glycoreceptors on the cell surface of antigen presenting cells, an important prerequisite for cellular activation leading to endocytosis and cytokine production. Furthermore, uptake of proteins followed by presentation of peptides thereof is the basis for efficient T-helper-cell activation, and thus the production of immune regulatory antibodies by B-cells or activation of regulatory T-cells. The allergy-protective oligosaccharides according to the invention can be synthetically produced. The substances can be produced under GMP conditions. The synthetic oligosaccharides of the invention are non-toxic.

P is preferably selected from carrier proteins like an albumin, such as, for example, human serum albumin (HSA) or functional fragments thereof, bovine serum albumin (BSA) or functional fragments thereof, ovalbumin or functional fragments thereof, keyhole-limpet hemocyanin (KLH), *Tachypleus tridentatus* hemocyanin (TTH), *Limulus polyphemus* hemocyanin (LPH), ExoU protein, and mixtures thereof. Furthermore P can be selected from the group of autoantigens, such as, for example, myelin oligodendrocyte glycoprotein, myelin basic protein, insulin, thyroglobulin, thyrotropin-receptor; and from the group of allergens, for example, FelD1, Betv1, Phlp1, 2, 5 and 6, Arah1, 2 and 3, Derp1 and 2.

As mentioned above, preferred is the arabino-oligosaccharide according to the present invention, wherein said arabino-oligosaccharide is synthetically produced. Preferably, the synthesis comprises a blockwise synthesis comprising condensating D-galactose and L-arabinose intermediates using an orthogonal protecting group pattern. The arabino-oligosaccharide according to the present invention can be fully or partially synthetically produced. One example of a synthetic procedure is without the use of enzymes. Another method comprises synthesis at least in part on (bound to) a solid surface, with a subsequent release from said surface.

Csávás et al. (in: Successful Combination of (Methoxydimethyl)methyl (MIP) and (2-Naphthyl)methyl (NAP) Ethers for the Synthesis of Arabinogalactan-Type Oligosaccharides, Synlett 2002, No. 6, 04 06 2002, pp 887-890) characterized the presumed epitopes of arabinogalactans, isolated from the extract of the cell-cultured *Echinacea purpurea*. Two oligosaccharides were synthesized. The whole synthetic route was based on the successful combination of the (methoxydimethyl)methyl (MIP) and the (2-naphthyl)methyl ether (NAP) protecting groups.

Fekete et al. (in: Synthesis of 3,6-branched arabinogalactan-type tetra- and hexasaccharides for characterization of monoclonal antibodies Carbohydrate Research 344 (2009) 1434-1441) describe the synthesis of tetra- and hexasaccharides built up from a β-(1→6)-linked galactopyranosyl backbone with arabinofuranosyl side chains at position 3 and with a 3-aminopropyl spacer related to arabinogalactans. These oligosaccharides were prepared for investigation of monoclonal antibodies raised against arabinogalactan proteins (AGPs) from pressed juice of *Echinacea purpurea*.

Another preferred aspect of the invention relates to the use of the arabino-oligosaccharide according to the present invention as a diagnostic tool and/or in in vitro or in vivo diagnosis. For these purposes the arabino-oligosaccharide according to the present invention (with or without being bound to a group P) can further comprise a detectable label, such as, for example, an enzymatic group, a dye or an isotope, streptavidin, avidin or maltose binding protein. Using the arabino-oligosaccharide according to the present invention as a diagnostic tool, for example tests can be performed in order to analyze and/or diagnose whether or not a subject or group of subjects shows an immune response, when compared with a control sample or subject.

Another preferred aspect of the invention relates to a pharmaceutical composition, comprising the arabino-oligosaccharide according to the present invention (with or without being bound to a group P), together with a pharmaceutically acceptable excipient and/or auxiliary agent.

A "pharmaceutical composition" is a composition suitable for administration to a mammal, in particular a human, in a medical setting. Preferably, a pharmaceutical composition is sterile and produced according to GMP guidelines.

The excipient can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferred to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound(s) in the required amount in the appropriate solvent with several other ingredients as described above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient plus any additional desired ingredient from a previously sterile-filtered solution thereof.

The pharmaceutical compositions as used herein may be formulated in a neutral or salt form. Pharmaceutically-acceptable salts include the acid addition salts (formed with the free amino groups of a protein) and are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation and in such amount as is therapeutically/prophylactically effective. The formulations are easily administered in a variety of dosage forms, such as injectable solutions, drug-release capsules, for inhalation, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic/prophylactic compositions is contemplated. Supplementary active ingredients can also be incorporated into the compositions.

The term "pharmaceutically acceptable" refers to molecular entities and compositions that do not produce an allergic or similar untoward reaction when administered to a mammal, such as a human. The preparation of an aqueous composition that contains a compound according to the present invention as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified. Another preferred mode of administration is by inhalation or as nose drops or nose spray.

Thus preferred is the pharmaceutical composition according to the present invention, wherein said composition is in the form of an aerosol, aqueous solution, suspension, lyophilisate, powder, tablet or suppository for oral, nasal, conjunctival, inhalative, subcutaneous, intraarticular, intraperitoneal, rectal or vaginal application or administration.

In another aspect, the composition according to the invention as described above can furthermore comprise at least one probiotic bacterium selected from the genera *Lactococcus* and *Bifidobacterium*. These bacteria may act to help in the preventive effect of the composition according to the invention against adverse immune reactions.

Yet another aspect of the invention then relates to a method for producing the arabino-oligosaccharide according to the present invention, comprising a blockwise synthesis comprising condensating D-galactose and L-arabinose intermediates using an orthogonal protecting group pattern. The arabino-oligosaccharide according to the present invention can be fully or partially synthetically produced. One example of a synthetic procedure is without the use of enzymes. Another method comprises synthesis at least in part on (bound to) a solid surface, with a subsequent release from said surface. Preferably, the method according to the present invention further comprises the step of attaching a proteinaceous group P to said molecule.

Yet another aspect of the invention then relates to a method for producing a pharmaceutical composition, comprising the method for producing the arabino-oligosaccharide according to the present invention, optionally further comprising the step of attaching a proteinaceous group P to said molecule, and admixing said arabino-oligosaccharide with a pharmaceutically acceptable excipient and/or auxiliary agent, and, optionally, with at least one probiotic bacterium selected from the genera *Lactococcus* and *Bifidobacterium*.

Yet another aspect of the invention then relates to the pharmaceutical composition according to the present invention for use in medicine. Yet another aspect of the invention then relates to the pharmaceutical composition according to the present invention for use in the prevention, protection against or treatment of allergic or chronical inflammatory diseases in mammals. Preferred is the prevention, protection against or treatment of a disease selected from IgE-depending Type I allergic diseases, Type IV allergic diseases, chronic inflammatory skin diseases and autoimmune diseases, such as, for example, hay fever, food allergy, asthma, urticaria, neurodermitis, atopic dermatitis, contact eczema, psoriasis, diabetes type 1 or 2, multiple sclerosis, systemic lupus erythematodes, rheumatoid arthritis, diseases of the thyroid gland, like Hashimoto Thyreoditis, and Graves' disease.

Since allergic reactions and respective diseases are found in many mammals, the compositions according to the present invention can also be used to successfully treat other mammals, such as, for example, pets, such as horses, dogs, and cats.

Yet another aspect of the invention then relates to a method for preventing, protecting against or treatment of allergic or chronical inflammatory diseases in a subject in need thereof, comprising administering an effective amount of the pharmaceutical composition according to the present invention to said subject.

The present invention shall now be described further in the following examples with reference to the accompanying figures, nevertheless, without being limited thereto. For the purpose of the present invention, all references as cited herein are incorporated by reference in their entities.

EXAMPLES

Methods

Synthesis of the Arabinogalactan (AG) Partial Structure Araf$_2$Galp$_5$ and the Control Structure Glcp$_{5+}$ An inventive oligosaccharide Araf$_2$Galp$_5$ was prepared by condensation of D-galactose and L-arabinose intermediates containing orthogonal protecting group pattern (acetyl, benzoyl, benzyl, triphenylmethyl, naphthylmethyl, etc.). For the condensation reaction different leaving groups were used (alkylthio, arylthio, fluoride, chloride, bromide, iodide, trichloroacetimidooxy, N-phenyl trifluoroacetimidooxy) in aprotic organic solvent (dichloromethane, acetonitrile, toluene, benzene, diethyl ether) in the presence of Lewis promoter (trimethyl trifluoromethanesulfonate, silver trifluoromethanesulfonate, N-iodo-succinimide) at adjusted temperature. Protecting groups of the synthesized oligosaccharide were removed by hydrolysis (base or acid in water), transesterification (by the Zemplen procedure, or with the aid of methanolic hydrogen chloride solution), reduction (using Pd or Pt in H$_2$ atmosphere) and by oxidation with 2,3-dichloro-5,6-dicyano-1,4-benzoquinone or cerium ammonium nitrate. The reducing end of the oligosaccharide bears an alkyl spacer (C$_3$-C$_8$) combined with an aromatic primary amine as anchor group precursor. The connection between the sugar residue and the spacer is an O-, S-, C-glycosidic linkage or phosphate diester linkage. Finally, the aromatic amine was transformed into an isothiocyanate suitable for coupling reaction with proteins.

Applying the same strategy as described above, the control structure Glcp$_{5+}$ was prepared. Instead of D-galactose or L-arabinose, D-glucose was used as starting material.

In an alternative embodiment, if the linker Z consists exclusively of an alkyl chain (e.g. n=1-8) this allows the introduction of Z at the beginning of the synthetic pathway as shown as an example below.

30

The synthesis of the higher L-arabino oligosaccharides and of the arabinogalactan oligosaccharide can be advantageously performed either stepwise or blockwise. The strategy using oligosaccharides as building blocks provided the best results concerning time, demand on material, and yield. The following building blocks were used:

-continued

-continued

BzO and NAPO=benzoyl and naphthyl protective groups, respectively.

Coupling of Oligosaccharides to Bovine Serum Albumin (BSA)

Low endotoxin albumin was solubilized in 0.1 M sodium carbonate buffer pH 8.5 to 10 mg/ml. Oligosaccharides were solubilized at 4 mg/ml in the same buffer. Equal volumes of both solutions were mixed. The reaction mixture was incubated for 2 h at 37° C. Afterwards the coupled protein was purified by size exclusion chromatography on Sephadex G-25. The molecular ratio of the number of pentasaccharide molecules coupled to one albumin molecule was determined by measuring sugar content in the sample via Resorcin test and determining protein concentration by Bradfords' assay.

Isolation of Arabinogalactan from *A. pratensis*

Freeze dried extracts from *A. pratensis* were dissolved at 100 mg/ml in isotonic sodium chloride solution. Subsequently, insoluble particles were removed by filtration through a 0.22 µm sterile filter. One ml was applied on a column Superdex 200 prep grade (16×60 cm) and eluted with 0.9% NaCl solution. Fractions with 1 ml volume were collected and the eluent was monitored continuously with a 280 nm detector. Arabinogalactan was detected in the collected fractions by an AG-specific sandwich ELISA. AG-containing fractions were concentrated to achieve a concentration of 1 mg/ml AG. This solution was mixed with 1 mg β-glycosyl Yariv reagent. The resulting precipitate was washed two times with 0.9% NaCl solution and dissolved by adding up to 2% (w/v) sodium dithionite and heating to 50° C. until the color changed from red to light yellow. Finally the solution was dialysed extensively against water.

Animals

Female BALB/c mice (Charles River, Sulzfeld, Germany) aged 7-8 weeks were used and acclimated to the animal facility for 14 days prior to experiments. Animals had access to food and water ad libitum. All experimental procedures were approved by the responsible animal ethics committees.

Sensitization and Airway Challenge

Mice were sensitized by intraperitoneal injection of 20 µg ovalbumin (OVA; GradeV; Sigma, St. Louis, Mo.) emulsified in 2.2 mg aluminum hydroxide (ImjectAlum; Pierce, Rockford, Ill.) in a total volume of 200 µl on days 1 and 14. On days 28 and 38 mice were challenged via the airways with 1% OVA aerosol for 20 min using a PARI-Boy aerosol generator.

Treatment of Animals with Substances

Mice were treated with the synthetic substances during the sensitization phase. Substances were administered intranasally in 50 µl of PBS. Mice were treated 14 times beginning on the day of the first OVA injection and the last treatment six days before the second OVA-aerosol challenge. Control groups were sensitized as described above and treated 14 times with phosphate buffered saline (PBS).

In Vitro Cytokine Production of Mouse Splenocytes

Spleens were harvested 3 days after the second aerosol challenge. Single cell suspensions were prepared by mechanical disruption and erythrocytes were lysed. Spleen cells were then cultured at a concentration of $5\times10^6$/ml in complete tissue culture medium (CTCM) (RPMI 1640 with 10% fetal calf serum (FCS), 2 mM L-glutamine, 100 U/ml penicillin, 100 µg/ml streptomycin, all from Biochrom, Berlin, Germany). To stimulate specific cytokine production OVA was added to a final concentration of 50 µg/ml. After 48 h of culture, supernatants were taken and stored at −80° C. until analysis. Levels of IL-5 and IL-13 were assessed by using optEIA kits (BD Biosciences, Heidelberg, Germany) according to the manufacturer's instructions.

Bronchoalveolar Lavage (BAL)

Three days after OVA challenge lungs were lavaged via a tracheal tube with 2×1 ml PBS, and leukocytes in the lavage fluid were counted. After centrifugation, BAL fluid was frozen for further analysis. Cytospin slides of BAL cells were stained with a fast staining procedure (HAEME-Schnellfärbung, Labor+Technik Eberhard Lehmann, Berlin, Germany), according to the manufacturer's instructions. The percentages of eosinophils, lymphocytes and macrophages in BAL samples were determined by light microscopy. At least 300 cells per sample were differentiated by a blinded investigator.

Measurement of Immnuoglobulins in Serum and BAL

Blood was collected by tail vein puncture two days after the second aerosol challenge. BAL was collected as described above. Levels of total IgE in serum or BAL fluid were determined by ELISA (Ebioscience). Levels of BSA-specific IgG1 were determined by indirect ELISA. Briefly, plates were coated with 50 µg/ml BSA followed by blocking with 1% low fat milk powder. The serum was diluted 1/100 in PBS and incubated on the BSA coated wells for 1 h, followed by detection of bound antibodies by alkaline phosphatase coupled rat anti mouse IgG1 (BDbiosciences).

Results

Synthetic Oligosaccharides can be Coupled to BSA

Figure 1:
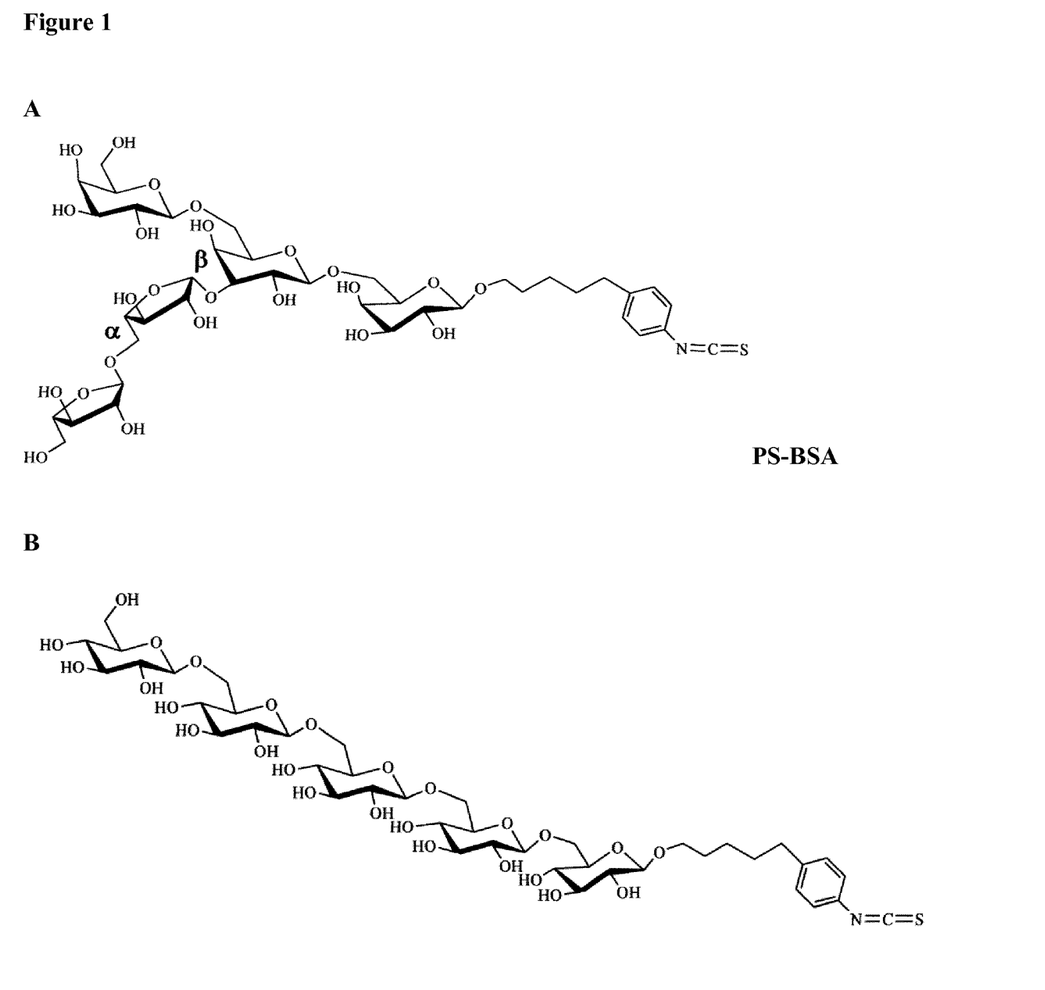
FIG. 1 shows carbohydrate structures that were synthesized stereoselectivly to mimic the configuration of arabinose and galactose containing epitopes in AG of grasses (A) (designated PS-BSA, when coupled to BSA). Control structures consisting of β-(1→6)-linked Glcp (B).

Pentasaccharides ($Araf_2Galp_3$) were synthesized to match the structure previously identified in AG of *A. pratensis*. As a control structure, a pentamer of glucopyranose ($Glcp_5$) was synthesized (See FIGS. 1A and 1B).

Figure 2:
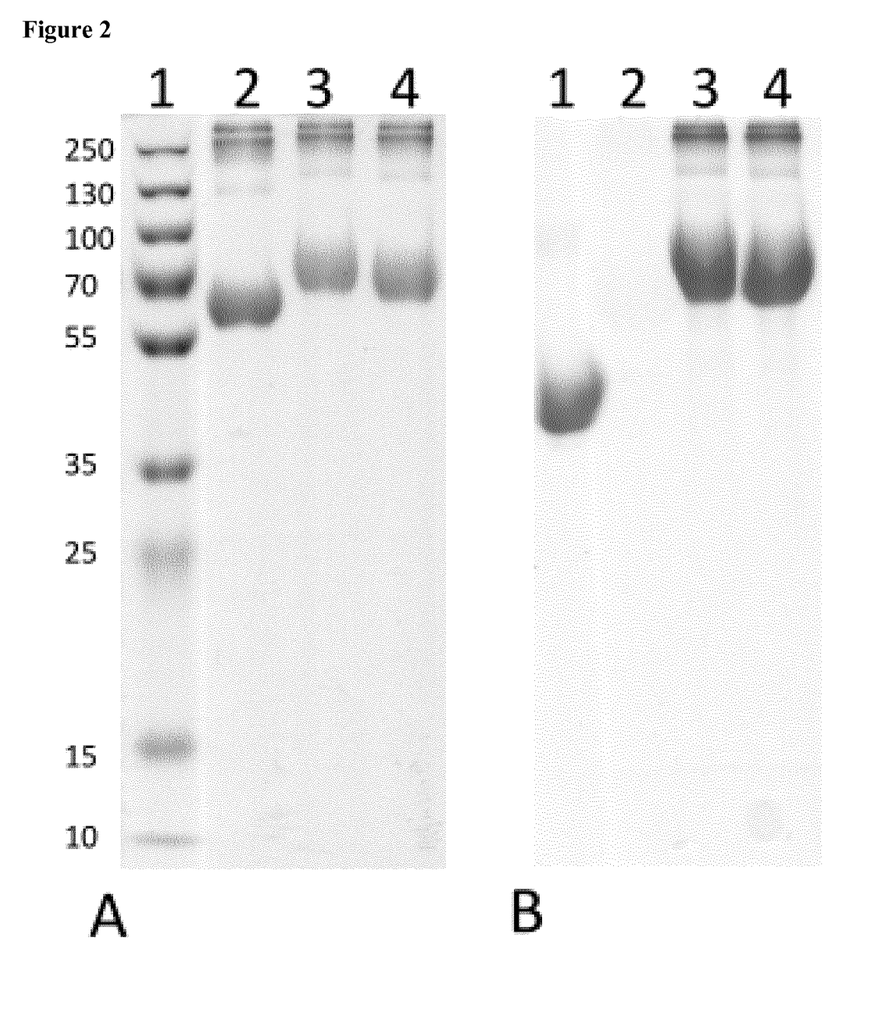
FIG. 2 shows un-conjugated BSA (lane 2), Glcp$_5$/BSA (lane 3) and Araf$_2$Galp$_3$/BSA (lane 4) stained with either Coomassie (A) or PAS (B). In lane 1 a pre-stained broad range marker is shown (A) or al-glycoprotein (44 kDa) in (B), respectively.

Both structures were composed to contain an amino reactive isothiocyanate group. Low endotoxin BSA was used as a carrier protein for these pentasaccharides. Conjugated BSA is shown in FIG. 2 as detected by Coomassie and PAS staining of proteins fractionated by SDS PAGE. Coomassie staining showed a prominent band at 66 kDa (lane 2 of FIG. 2A). As expected molecular mass of BSA conjugated to either $Glcp_5$ (lane 3) or $Araf_2Galp_3$ (lane 4) increased. These conjugates also showed PAS positive staining as shown in FIG. 2B whereas un-conjugated BSA did not (lane 2, FIG. 2B).

By measurement of carbohydrates and protein concentration in the glycoconjugates the ratio of oligosaccharides to protein was determined to be 10 mol/mol Araf$_2$Galp$_3$/BSA and 11 mol/mol for Glcp$_5$/BSA.

Araf$_2$Galp$_3$ has Allergy Protective Activity When Coupled to BSA

Figure 3:
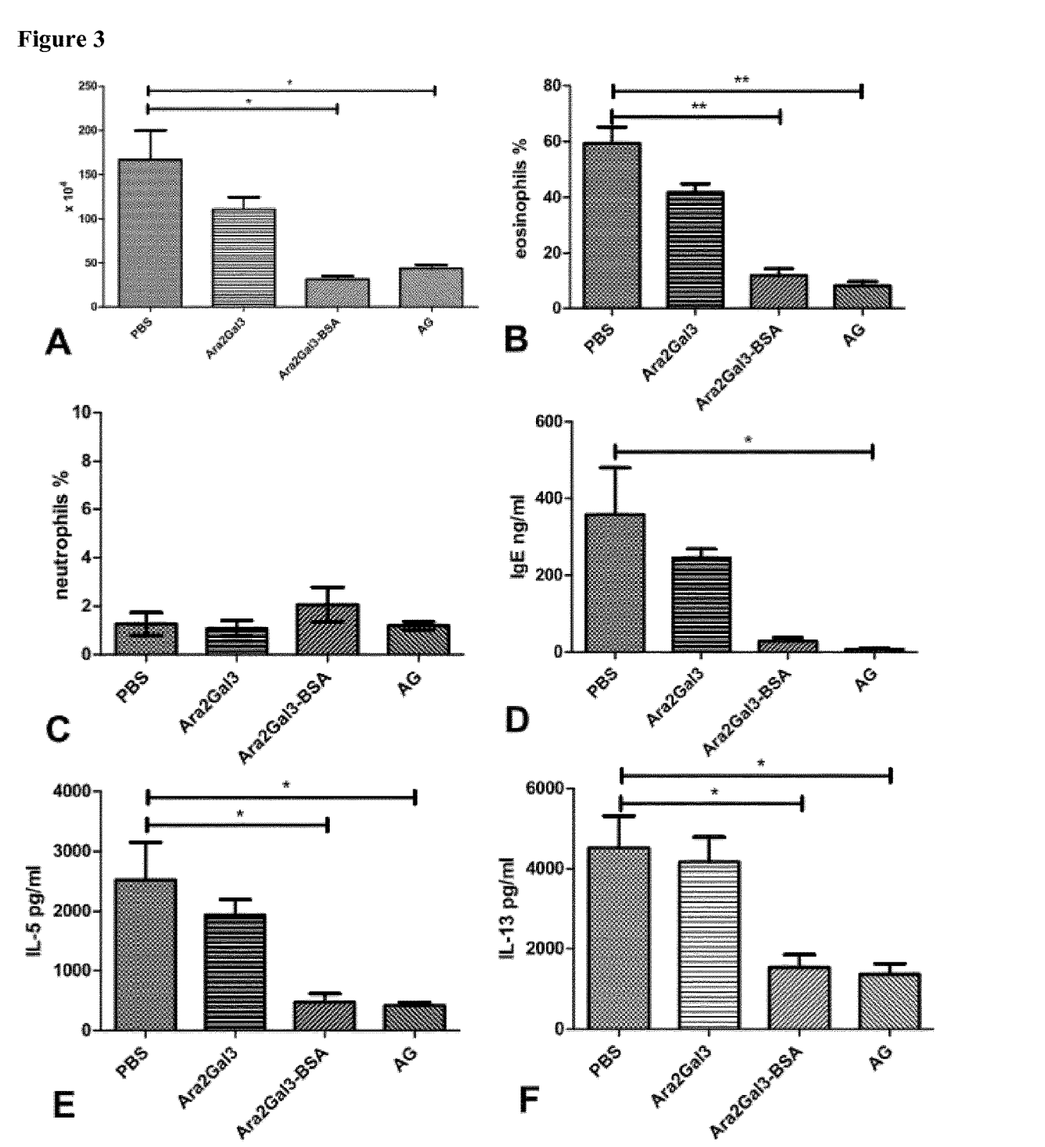
FIG. 3 shows the result of the experiments where mice were sensitized with OVA/Alum by two i.p. injections. Afterwards mice were challenged with OVA aerosol for two times. During the sensitization and challenge phase mice were treated by i.n. administration of the indicated substances. Total cells in BAL were counted (A) and subpopulations differentiated by light microscopy; percentage of eosinophilic granulocytes (B) and neutrophilic granulocytes (C) are shown. IgE was measured in BAL fluid (D). Production of IL-5 (E) and IL-13 (F) was determined in spleen cell supernatants after re-stimulation of cells with OVA. One way ANOVA was used to analyze the data for statistical differences. *$P<0.05$ and $P<0.01$

To test whether Araf$_2$Galp$_3$ alone or covalently coupled to the carrier protein albumin shows allergy protective activity comparable to arabinogalactan isolated from *A. pratensis* we have tested these substances in a mouse model using systemic sensitization with OVA/Alum. FIG. 3 shows the results of the animal experiment.

Treatment with Araf$_2$Galp$_3$-BSA led to reduced Th2 response as measured by in vitro production of IL-5 and IL-13 by spleen cells resulting in reduced eosinophilic airway inflammation and IgE production. Also the goblet cell metaplasia was reduced as determined in lung sections. Efficacy of treatment was comparable to AG shown to be allergy protective in former studies. Treatment with Araf$_2$Galp$_3$ alone was not able to reduce these parameters significantly.

These results show that Araf$_2$Galp$_3$-BSA leads to protection from allergic disease when administered intranasally during sensitization.

Araf$_2$Galp$_3$-BSA has Superior Allergy Protective Activity as Compared to Another Glycoconjugate In order to test whether the observed allergy protective activity relies on the specific structure of Araf$_2$Galp$_3$-BSA or is also observable with other oligosaccharides coupled to BSA we synthesized apentamer of glucose Glcp$_5$. This glycostructure was also coupled to BSA and compared to Araf$_2$Galp$_3$-BSA in a mouse model of allergic airway inflammation.

Figure 4:
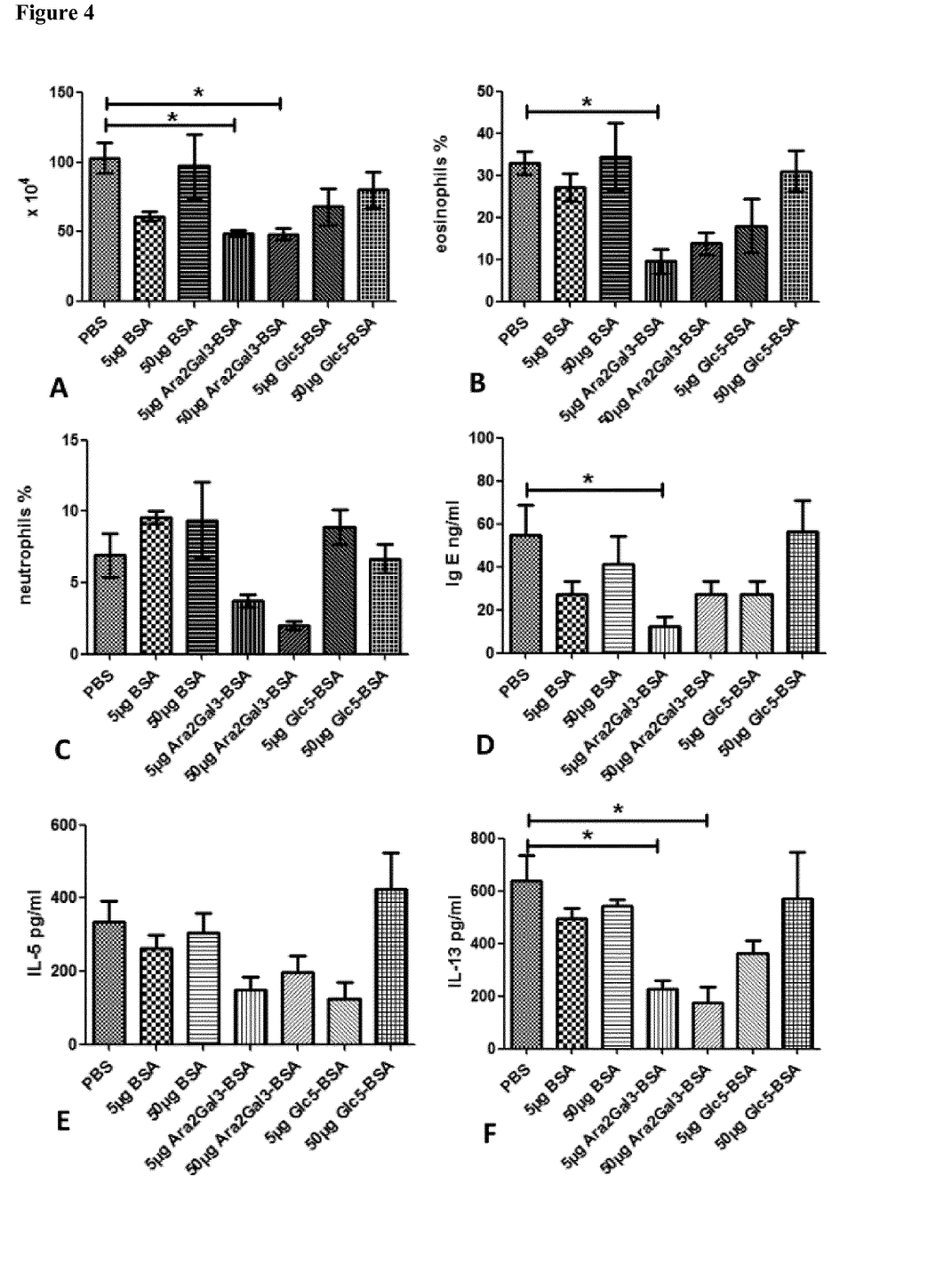
FIG. 4** shows the result of the experiments where mice were sensitized with OVA/Alum by two i.p. injections. Afterwards mice were challenged with OVA aerosol for two times. During the sensitization and challenge phase mice were treated by i.n. administration with two different amounts of the indicated substances. Total cells in BAL were counted (A) and subpopulations differentiated by light microscopy; percentage of eosinophilic granulocytes (B) and neutrophilic granulocytes (C) are shown. IgE was measured in BAL fluid (D). Production of IL-5 (E) and IL-13 (F) was determined in spleen cell supernatants after re-stimulation of cells with OVA. One way ANOVA was used to analyze the data for statistical differences. *$P<0.05$ and $P<0.01$

As shown in FIG. 4, only treatment with Araf$_2$Galp$_3$-BSA led to significant reduction of allergic airway inflammation, Th2 cytokine production and allergic sensitization. These results show that allergy protective activity of Araf$_2$Galp$_3$-BSA depends on the specific composition of the glycoepitope and is not due to unspecific glycosylation of BSA.

Araf$_2$-BSA has Allergy Protective Activity

Figure 5:
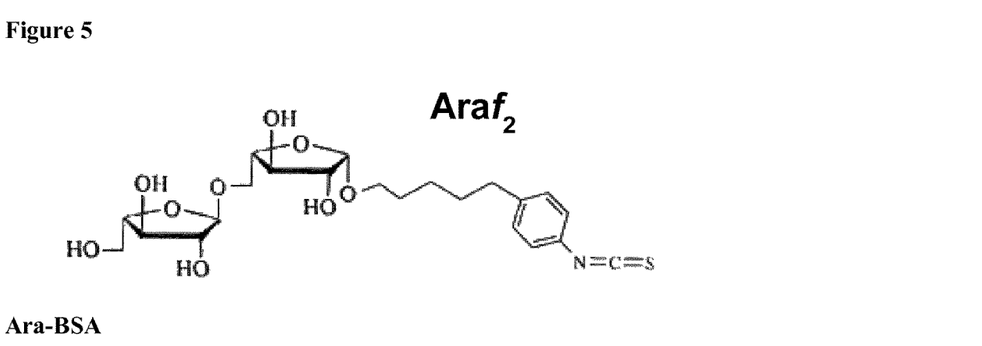
FIG. 5** shows the carbohydrate structure of a preferred L-arabino-oligosaccharide (Araf$_2$-BSA) (designated Ara-BSA, when coupled to BSA).
Figure 6:
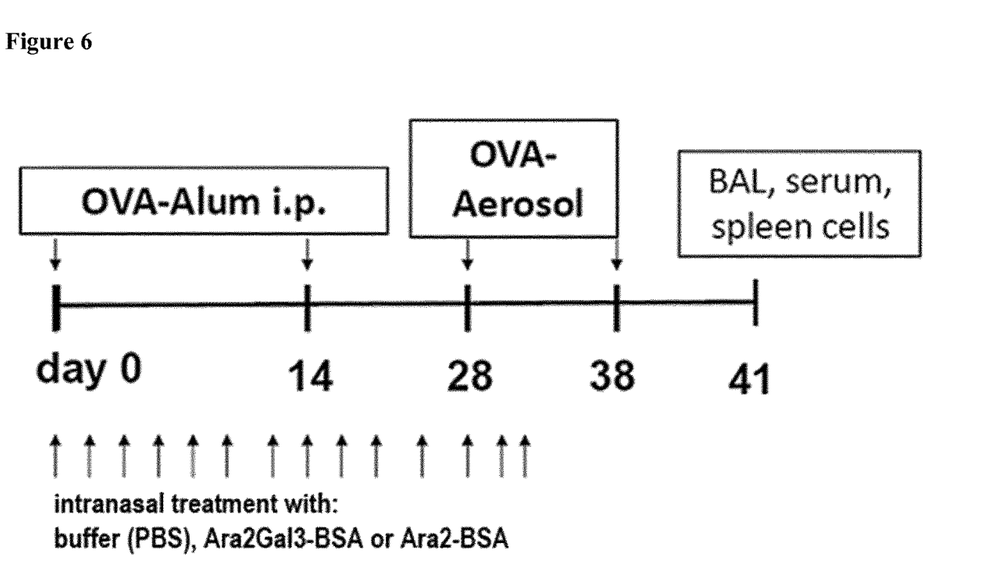
FIG. 6 shows the intranasal treatment schedule using the molecules PS-BSA (see FIG. 1) or Ara-BSA (FIG. 5).

In order to test whether the observed allergy protective activity relies on the di-arabinose structure we synthesized Araf$_2$ as shown in FIG. 5. This glycostructure was also coupled to BSA and compared to Araf$_2$Galp$_3$-BSA in a mouse model of allergic airway inflammation (for a schematic overview please refer to FIG. 6).

Figure 7:
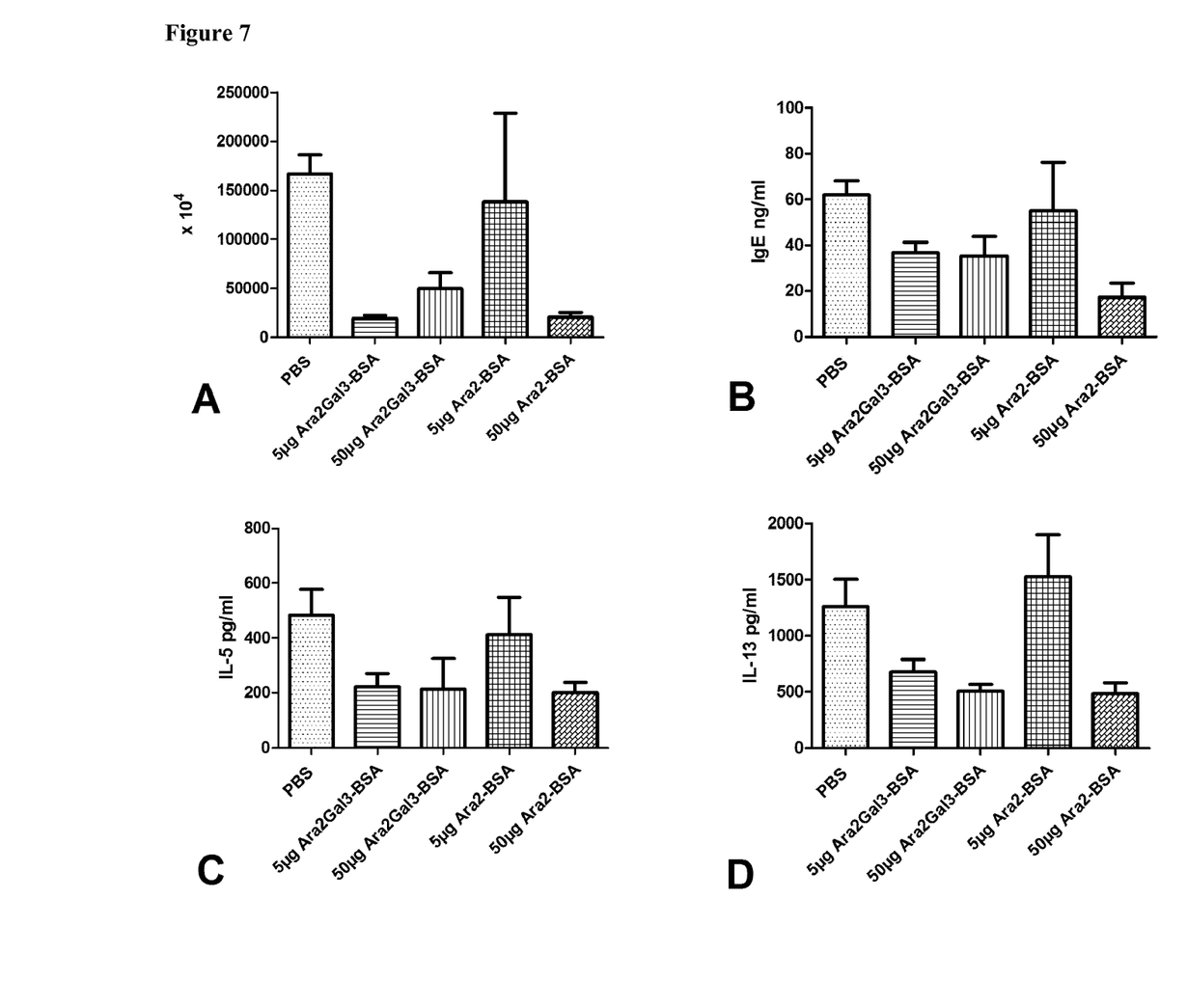
FIG. 7 shows the results of the treatment using Ara-BSA in the mouse model for asthma. A) number of eosinophil granulocytes in the respiratory system. B) concentration of IgE in the respiratory system. C and D) concentration of Th2 cytokines in the supernatants of spleen cells that were restimulated with OVA.

As shown in FIG. 7, treatment with Araf$_2$-BSA led to significant reduction of infiltration of eosinophilic granulocytes, Th2 cytokine production and allergic sensitization (IgE). The allergy protective activity is comparable to Araf$_2$Galp$_3$-BSA but only when Araf$_2$-BSA was given in an amount of 50 μg.

Literature as Cited

Braun-Fahrländer C, et al. Environmental exposure to endotoxin and its relation to asthma in school-age children. New Engl J Med 2002; 347:869-77.

Csávás M, et al. Successful Combination of (Methoxydimethyl)methyl (MIP) and (2-Naphthyl)methyl (NAP) Ethers for the Synthesis of Arabinogalactan-Type Oligosaccharides. Synlett 2002; 6:887-90.

Fekete A, et al. Synthesis of 3,6-branched arabinogalactan-type tetra- and hexasaccharides for characterization of monoclonal antibodies. Carbohydrate Research 2009; 344: 1434-41.

Peters M, et al. Inhalation of stable dust extract prevents allergen induced airway inflammation and hyperresponsiveness. Thorax. 2006 February; 61(2):134-9.

Peters M, et al. Arabinogalactan isolated from cowshed dust extract protects mice from allergic airway inflammation and sensitization. J. Allergy Clin. Immunol. 2010; 126(3): 648-56.e1-4.

Riedler J, et al. Exposure to farming in early life and development of asthma and allergy: a cross-sectional survey. The Lancet 2001; 358:1129-33.

The invention claimed is:

1. A method for the prevention, protection against or treatment of an allergic or chronical inflammatory disease in a mammal wherein said method comprises administering to the mammal a composition comprising an L-arabino-oligosaccharide according to the following general formula (I)

wherein arabino-configured monosaccharides are either α- or β-connected,

R is selected from a linker group Z according to the following formula wherein X is selected from S, CH$_2$, and PO$_4^-$; and wherein Y is selected from CO$_2$H, wherein V is a C$_1$-C$_6$ alkyl or aryl residue; a D-galactose residue comprising Z, and a β-(1→6)-linked D-galactose oligosaccharide comprising Z, and wherein Z is optionally coupled to a proteinaceous group P, and pharmaceutically acceptable salts thereof.

2. The method according to claim 1, wherein said disease is selected from IgE-depending Type I allergic diseases, Type IV allergic diseases, chronic inflammatory skin diseases and autoimmune diseases.

3. The method, according to claim 2, wherein the disease is selected from hay fever, food allergy, asthma, urticaria, neurodermitis, atopic dermatitis, contact eczema, psoriasis, diabetes type 1 or 2, multiple sclerosis, systemic lupus erythematodes, rheumatoid arthritis, and diseases of the thyroid gland.

4. The method, according to claim 3, wherein the disease of the thyroid gland is selected from Hashimoto Thyreoditis and Graves' disease.

5. The method according to claim 1, wherein R is selected from

6. The method according to claim 1, wherein the L-arabino-oligosaccharide has the following general formula (II)

and pharmaceutically acceptable salts thereof.

7. The method according to claim 6, wherein the L-arabino-oligosaccharide has the following formula and pharmaceutically acceptable salts thereof.

8. The method according to claim 1, wherein P is selected from an albumin, keyhole-limpet hemocyanin (KLH), *Tachypleus tridentatus* hemocyanin (TTH), *Limulus polyphemus* hemocyanin (LPH), autoantigens, allergens and mixtures thereof.

9. The method according to claim 1, wherein said arabino-oligosaccharide is synthetically produced.

10. The method according to claim 1, wherein said arabino-oligosaccharide further comprises a detectable label.

* * * * *